United States Patent
Keyes et al.

(10) Patent No.: US 6,234,014 B1
(45) Date of Patent: May 22, 2001

(54) METHOD AND APPARATUS FOR ANALYZING GAS FLOW THROUGH CONDUITS

(75) Inventors: John J. Keyes; George A. Kuipers, both of Oak Ridge; DeForest F. Smith, Kingston, all of TN (US)

(73) Assignee: The United States of America as represented by the United States Department of Energy, Washington, DC (US)

(*) Notice: Subject to any disclaimer, the term of this patent is extended or adjusted under 35 U.S.C. 154(b) by 0 days.

(21) Appl. No.: 03/548,556

(22) Filed: Nov. 22, 1955

(51) Int. Cl.[7] ............................. G06K 7/16; G06F 17/60; G01F 13/00
(52) U.S. Cl. ..................... 73/196; 73/23.32; 73/118.1
(58) Field of Search .................. 73/27, 23, 30, 73/196, 167, 112, 421, 421.5, 262, 23.32, 118.1; 99/1

(56) References Cited

U.S. PATENT DOCUMENTS 2,721,578 * 10/1955 Pouppirt .............................. 73/118.1
2,734,381 * 2/1956 Jacobson ............................... 73/197
2,751,777 * 6/1956 Cherrier ................................. 23/32

* cited by examiner

Primary Examiner—Nelson Moskowitz
(74) Attorney, Agent, or Firm—Emily G. Schneider; Paul A. Gottlieb

(57) ABSTRACT

The method of measuring the mixing efficiency in porous tubes comprising generating gas waves the composition of which at substantially constant total flow rate and pressure varies sinusoidal with time, causing said gas waves to flow through a section of said tubing from inlet to outlet, periodically sampling the gas waves in said tubing at a first point at the peak amplitude of the concentration of a first gas, sampling said waves at a second point at the peak amplitude of the concentration of a first gas, measuring the concentration of said first gas in said mixture in both said samples, and deriving and recording the difference in said concentration for each sampled wave, the difference of said concentrations at said peak amplitudes being a measure of the mixing efficiencies of said tube.

3 Claims, 2 Drawing Sheets

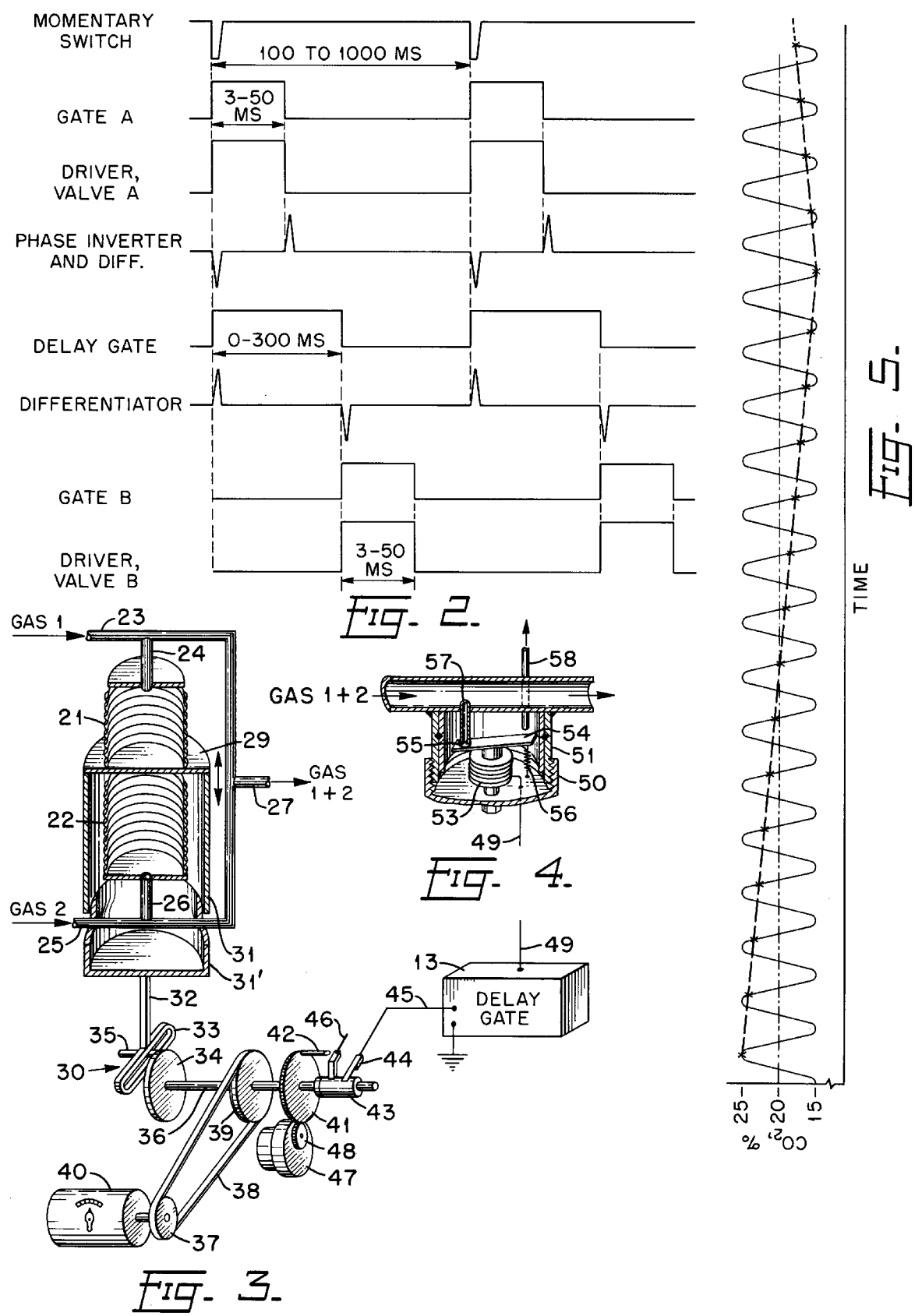

METHOD AND APPARATUS FOR ANALYZING GAS FLOW THROUGH CONDUITS

The present invention relates to a dynamic response method of analyzing the flow of a binary gas mixture through conduits of any desired configuration, and more especially to a novel method of and apparatus for determining the mixing efficiency and certain other related physical characteristics of conduits, with particular reference to open tubes.

In design of equipment for separation and purification of fluid mixtures, such as the separation of uranium-238 from uranium-235 by the process of gaseous diffusion, it is important to know certain physical characteristics of the open porous-walled tubes carrying the binary gas mixture. Of particular interest is the knowledge of the dependance of the radial mass transfer rate upon such factors as the properties of the gases, flow rates, characteristics of the inner tube wall, and so forth. One measure of this mass transfer rate is obtained from the "mixing efficiency" of the tubes. For porous tubes, this efficiency may be defined as the ratio of the average concentration of light component at the center of the stream minus the concentration of light component at the outside of the wall to the average concentration of light component at the inside of the wall minus the concentration of light component at the outside of the wall. In the porous tubes used in gaseous diffusion operations, flow through the tubes produces a layer of gas adjacent the tube wall which is depleted in the lighter element of the binary mixture, and this layer tends to prevent diffusion from the central core of the flowing stream of gas through the tube walls. A measure of the effectiveness of a tube for diffusion separation, therefore, is the effective thickness of that gas layer or film. Similarly, in heat exchanger design, turbulence promoters are provided in the non-porous, open tubes to mix the cool central core of air with the hot outer layer contacting the tube wall so that the entire volume of air may be heated, rather than only a thin outer layer. The efficiency with which the various turbulence promotion means effect the mixing of inner and outer portions of the air column flowing through the non-porous tubes may also be termed the "mixing efficiency."

Conventional methods of measuring the mass transfer characteristics, above described, heretofore involved either steady-state removal from or addition to a gas stream of a component by a transfer from or to another adjacent liquid phase. Fundamental knowledge of the effect of individual variables is often difficult to obtain by these methods, because conditions on both the gas and liquid sides influence the results obtained. Moreover, the range of compositions which can be studied is limited by solubility and vapor pressure considerations, extra equipment is required to circulate the liquid in contact with the gas, and compositions vary along the fluid column so that an average composition difference must be defined.

With a knowledge of the problems involved in obtaining physical measurements of the character described by prior methods, it is an object of the present intention to provide a method of and apparatus for analyzing a binary fluid mixture flowing through a conduit to obtain mass transfer characteristics without the difficulties and limitations associated with prior methods, while additionally obtaining data not otherwise obtainable. A further object of the invention is to provide a novel method and mans for determining the mixing efficiency of a porous tube. Yet another object of the invention is to provide a method of and means for determining the effectiveness of turbulence promoters in mixing fluid streams in non-porous open tubes. A principal object of the invention is to provide a novel method of analyzing gas flow through tubes by cyclically mixing two gases to create a fluid stream of cyclically varying composition, directing said stream down a length of the tube, sampling a wave in the stream near the input and output ends of the tube, and determining the difference in the peak concentrations of one gas in said wave between inlet and outlet, or determining the corresponding phase shift, if any, in said peak concentrations. Other objects and advantages of the invention will become apparent from the following detailed description of a preferred embodiment thereof, when read in conjunction with the appended drawings, in which:

FIG. 2 shows wave-forms of electrical operating signals at various points in FIG. 1;

FIG. 3 illustrates a means for generating a sinusoidal composition wave at constant total flow rate and pressure;

FIG. 4 illustrates the sample obtaining means shown in FIG. 1 in detail; and FIG. 5 is a wave diagram illustrating the sampling of a gas stream of varying compositions.

Figure 1:
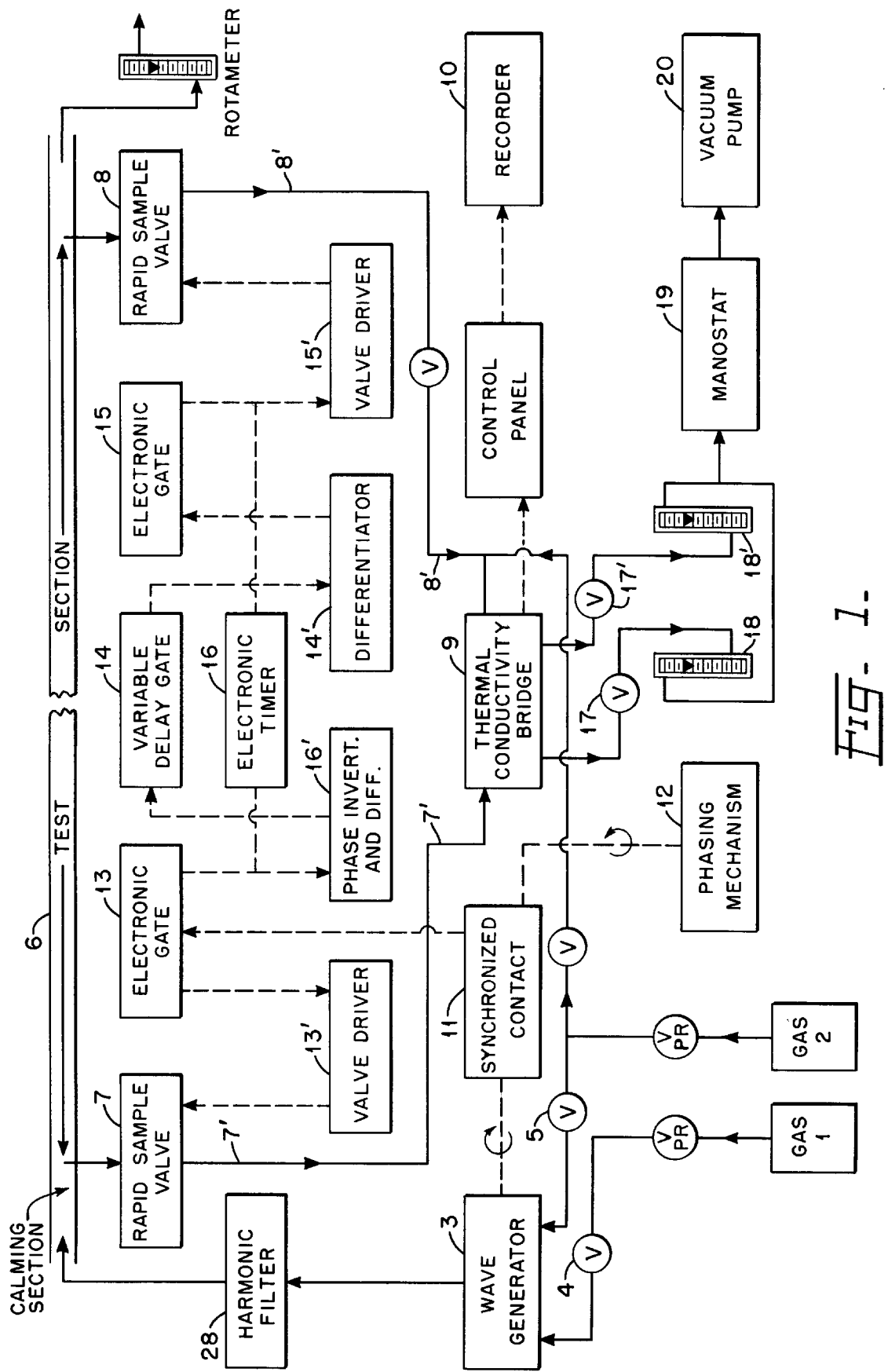
FIG. 1 is a schematic drawing of a system for obtaining the characteristic measurements described above.

According to the present invention, binary gas waves are generated by any suitable means, the composition of which waves at substantially constant total flow rate and pressure varies sinusoidally with time, and these waves are admitted to the inlet portion of a tube to be tested. A first sample of the gas is taken near the inlet and from any wave and a second sample is taken near the outlet end of the tube after a selected time delay. The peak amplitude concentration of a single component of the gas is measured for each sample, and the two resulting signals are combined to produce an output dependent upon either the magnitude difference or the phase shift of the peak amplitudes of the signals. The sampling is repeated continuously, but at a different frequency from that of the generated wave, so that the sampling point completely traverses the wave at a frequency sufficiently low for the analytical equipment to follow.

Referring now to FIG. 1, one form of apparatus suitable for carrying out the above method in relation to an open tube may comprise sources 1, 2 of the two gases to be sized and a gas mixer or wave generator 3 to which the gases are admitted through pressure regulators VPR, control valves 4, 5 and the connected gas lines, shown by solid lines. The generator, to be described in detail later, combines the two gas streams into a feed stream, the concentration of which varies sinusoidally about a selected base concentration, and delivers the feed stream to the input or calming section of tube 6. Near the intake end, a rapid sample valve 7 is provided to remove a sample of the gas from the tube 6, while near the output end an identical sample valve 8 is provided for the same purpose. These sample valves are not of the continuous type, but provide for intermittent sampling when actuated by electrical pulses. Outputs are taken from the two sample valves through gas flow lines 7', 8' to opposite sides of a commercial thermal conductivity bridge 9, such as the N.R.L. Model of the Go-Mac Company, the output of which bridge is determined by the relative amplitudes and phase relationships of the two input waves received. If the waves are exactly in phase, the recorder 10 connected across the bridge will indicate the amplitude difference directly. The dashed lines indicate electrical connections. Means are provided for adjusting and measuring the delay in opening the two samplers required to sample a moving gas wave at the same point by both input and output samplers. From this delay the phase shift may be computed, knowing the velocity of the gas and the distance between the samplers.

The sample valves are controlled by an electronic control system adapted to control accurately and indicate the time delay between opening of the two valves and also the time each remains open. Reference is made to FIG. 2 for the preferred waveforms of electrical signals associated with the control system. A negative pulse is generated by the phasing mechanism 12 and delivered to electronic gate circuit 13, which produces a positive pulse of duration adjustable between 3 and 50 milliseconds. Valve driver 13' amplifies the positive pulse and causes solenoid valve 7 to open. The positive pulse also is applied from gate 13 to a phase inverter stage and differentiating network 16', which produces a negative spike at the time of the phasing pulse and a positive spike at the time gate 7 opens. Delay gate circuit 14 is responsive only to negative pulses, and generates a positive output signal at a time corresponding to the phasing pulse. Provision is made for adjusting the time length of the positive signal from 0 to 300 milliseconds to achieve the desired delay. The delayed signal is differentiated in network 14' to produce positive and negative spikes which are delivered to gate 15, which is responsive only to negative signals. Therefore gate 15 produces its positive output signal at a time corresponding to the opening of gate 7, the signal being adjustable in duration from 3 to 50 milliseconds. Driver 15' amplifies the signal and opens solenoid valve 8 at a time delayed from the opening of valve 7 by an amount set by adjusting the delay gate 14. The adjustment is made so that the wave sampled by valve 7 is also sampled by valve 8; that is, the samplers are in phase. Proper setting may be made by changing the delay until a minimum signal appears on the recorder, indicating that each wave sampled is sampled at the same point by both samplers.

Timer 16 may not used to measure the above delay, and ray be any commercial time interval measuring instrument. The electronic gates, driver-amplifiers, and differentiating networks may be of conventional design such as are well-known to the art, their specific design forming no part of our invention.

Referring now to FIG. 3, the wave generator and associated synchronizer may comprise two axially-aligned standard bellows 21, 22 which are rigidly joined base to base. Bellows 21 is vented to supply line 23 through a rigid transfer line 24 connected into the outer end of the bellows, while bellows 22 is similarly connected to supply line 25 through rigid transfer line 26. The supply lines 23, 25 join downstream of the generator to form the gas supply line 27 extending into the harmonic filter 28 of FIG. 1. The bases of both bellows are joined to plate 29, which forms the top of moveable tubular member 31. Cup-shaped member 31' is mounted in fixed relation to supply line 25 and engages the inner surface of member 31 in telescoping relation. Arm 32 is joined to plate 29 at its upper extremity and is attached to a scotch-yoke mechanism 30 to impart a reciprocating action to the bellows. The gas output thus provided in line 27 by alternately expanding and contracting each bellows is at substantially constant total pressure, but varies sinusoidally in composition.

The drive mechanism includes the cylindrical housing 31, arm 32 having at one end slotted member 33, and wheel 34 having crank 35 rigidly mounted near the circumference thereof. The wheel is mounted on shaft 36 which is turned by drive wheel 37, belt 38, wheel 39, and variable speed drive motor 40. Gear wheel 41 is carried on shaft 36, but does not turn therewith and is provided with a phasing contact 42 mounted rigidly near the circumference thereof and extending parallel to the drive shaft. Slip ring 43 is mounted on the shaft adjacent the gear wheel and is contacted by finger 44, which is electrically connected through lead 5 to the electronic gate 13. A contact 46 mounted on the drive shaft rotates therewith and is arranged to contact the phasing contact. A motor 47 drives a gear wheel 48 which is meshed with gear wheel 41 to turn the latter.

In operation of the generator and its synchronizer, an output pulse is produced on lead 49 to operate the samplers each time the rotating contact 46 makes electrical connection with the phasing contact 42, which connection occurs once during each revolution of the gear wheel. Since the contact 46 is driven by the same shaft 36 which drives the skotch-yoke drive, connection is made with the contact 42 and a pulse is generated on lead 49 to open the samplers once during each cycle of the generator. The constant speed clock motor, called the scanner, through its small gear, may drive the gear wheel 41 and move the phasing contact 42 at a selected rate. The speed of rotation of the clock motor and that of the drive shaft are preferably so arranged that the phasing contact is advanced slightly during each revolution of the drive shaft so that it contacts the rotating contact 46 at intervals just greater than 360°.

The resulting sampling is illustrated graphically in FIG. 5, where the sinusoidal solid line represents the amplitude of the peak concentration of one gaseous component and the points marked by "x" indicate the times when samples are withdrawn. It may be seen that these times are slightly greater than 360° apart so that slightly different concentrations of the gas mixture will be obtained upon each successive opening of the samplers. The dashed line connecting the points "x" may be seen to be sinusoidal in nature, but of a frequency substantially smaller than that of the gas wave. If, for example, the gas concentration varies at the rate of 10 cycles per second, the synchronizer may be adjusted to advance contact 42 by 6 degrees per second, thus completing a cycle of scanning in 60 seconds, one scan cycle being completed when a sample is withdrawn at the same point in the gas wave cycle as when the first sample was taken. At such rates, the concentration of gas samples fed to the analyzers still vary sinusoidally, but at a rate of only one cycle per minute, rather than 10 cycles per second. Samples varying at this relatively slow rate can be readily and accurately analyzed by thermal conductivity means and recorded, whereas samples varying at the faster rate could not be accurately analyzed with instrumentation now known. A further advantage in the described sampling method is that it is not necessary to know precisely then peak concentrations will occur at the sampling points and to provide accurate timers for sampling at those times in order to obtain accurate measurement of those peak amplitudes, but instead representative, slowly changing samples are obtained in which the peak can be readily observed and measured.

Referring now to FIG. 4, a preferred form of the rapid sampler valve and its connections to the tube section under test are illustrated. The valve may comprise a cup-shaped, internally threaded housing 50 which engages a correspondingly threaded upper housing 51, the upper circumference of which is joined to the tube section by welding or soldering. Inside the housing is mounted a miniature relay 53 provided with relay arm 54. On one end of the arm a rubber valve seat 55 is provided, while at the other end a spring 56 is attached to the housing 50. A small tube 57 forming the sample inlet probe is inserted through a corresponding aperture in the tube wall and extends slightly therethrough, being rigidly fastened to the outside tube surface by soldering. An outlet tube 58 is provided from inside the housing 51 to the thermal conductivity cell.

In operation of the valve, spring tension normally holds the rubber seat 55 against the open end of the inlet tube 57 so that no gas enters the valve housing therethrough. The thermal conductivity cell is at a lower pressure than that existing inside the valve housing, so that any gas admitted will tend to flow through the housing and its outlet tube into the cell. When an electrical pulse is received from the electronic gate along lead 49, the relay is energized, pulling down the arm and disengaging the seat from the inlet probes allowing gas from the tube to enter the probe, whence it flows through the housing and exits through the outlet tube to the thermal conductivity cell. At the end of the pulse from the gate, the relay drops out and the spring forces the rubber seat against the inlet probe, closing it to prevent further removal of gas from the tube section.

It will be apparent to those versed in the art that we have provided a novel method of determining mass transfer characteristics of fluids in conduits such as mixing tanks, tubes, or apertures of various geometrical shapes.

Having described our invention, what is claimed as novel is:

1. The method of measuring the mixing efficiency in porous tubes comprising generating gas waves the composition of which at substantially constant total flow rate and pressure varies sinusoidally with time, causing said gas waves to flow through a section of said tubing from inlet to outlet, periodically sampling the gas waves in said tubing at a first point at the peak amplitude of the concentration of a first gas, sampling said waves at a second point at the peak amplitude of the concentration of said first gas, measuring the concentration of said first gas in said mixture in both said samples, and deriving and recording the difference in said concentration for each sampled wave, the difference of said concentrations at said peak amplitudes being a measure of the mixing efficiencies of said tube.

2. The method of making physical measurements of the character described comprising generating binary gas wave the composition of which at substantially constant total flow rate and pressure vary sinusoidally with time at a first frequency, causing said gas wave to flow through a section of tubing from inlet to outlet, periodically withdrawing samples from a first point in said tubing at a second frequency and out of phase with said first frequency, withdrawing samples from a second point in said tubing a selected interval after said first withdrawals, said interval being such that said samples are withdrawn at said first and second points from the same point on the same gas wave, deriving an output signal proportional to the differences in concentration of a selected gas component in corresponding samples obtained from said first and second points, and continuously recording said output signal during the periodic sampling of said waves.

3. Apparatus of the character described comprising a source of a first gas, a source of a second gas, first and second bellows joined end to end, first and second gas lines communicating between respective gas sources and respective opposite ends of said joined bellows, a section of tubing, a third gas line coupled to both said first and second lines and communicating with the inlet end of said tubing, first and second probes extending through said tubing walls near said inlet and outlet ends of said tubing, respective means for opening and closing said probes responsive to electrical signals, a drive shaft, means for rotating said shaft at a selected constant rate, means driven by said shaft for imparting reciprocating motion to the joined ends of said bellows to generate a gas wave in said third line, a gear carried by said shaft and provided with a contact member, separate drive means for rotating said gear about said shaft at a rotational frequency different from that of said shaft, a second contact member rotated by said shaft and adapted to contact said first contact member, and electrical circuit means for energizing said valves including a source of direct current, a valve actuating coil, and a switch circuit including a contact brush and a slip ring mounted on said shaft in contact with said brush; said second contact, said first contact, said gear wheel, and said gear wheel drive means being connected in electrical series circuit with said source for energizing said coils only when electrical contact is made between said first and second contacts.

\* \* \* \* \*